United States Patent [19]
Barak

[11] Patent Number: 5,961,488
[45] Date of Patent: Oct. 5, 1999

[54] SYSTEM AND METHOD FOR ADMINISTERING TWO LIQUIDS

[75] Inventor: Swi Barak, Caesarea, Israel

[73] Assignee: Nestec S.A., Vevey, Switzerland

[21] Appl. No.: 09/031,210

[22] Filed: Feb. 26, 1998

[30] Foreign Application Priority Data

Apr. 11, 1997 [IL] Israel ........................................ 120654

[51] Int. Cl.⁶ .................................................... A61M 5/14
[52] U.S. Cl. ................................ 604/80; 604/81; 604/30; 604/246
[58] Field of Search ................................ 604/80, 81, 123, 604/122, 151–153, 247, 248, 30, 32, 33, 246

[56] References Cited

U.S. PATENT DOCUMENTS

| | | | |
|---|---|---|---|
| 4,512,764 | 4/1985 | Wunsch | 604/80 |
| 5,032,112 | 7/1991 | Fairchild et al. | 604/151 X |
| 5,356,375 | 10/1994 | Higley | 604/80 X |
| 5,584,671 | 12/1996 | Schweitzer, Jr. et al. | |
| 5,643,205 | 7/1997 | Utterberg | 604/80 |

*Primary Examiner*—John D. Yasko
*Attorney, Agent, or Firm*—Hill & Simpson

[57] ABSTRACT

A flow set which enables the sequential administration of two liquids from a pair of containers to a patient. The flow set has a pair of valve assemblies each in communication with a container. Each valve assembly has three ports communicating through a communication chamber; an inlet port being sealed with a first one-way valve allowing flow of liquid through it only into the chamber, an outlet port being sealed with a second one-way valve allowing flow of liquid through it only out of the chamber, and a pump communication port. A pair of inlet tubing segments each connect a container to the inlet port of a valve assembly. A connecting tubing segment connects the pump communicating ports of the two valve assemblies. An outlet tubing segment connects to the outlet port of each valve assembly for delivery of the liquid to the patient. A pump is connected to the connecting tubing segment. By reversing the pumping direction of the pump, liquid may be sequentially draw from one container or the other.

5 Claims, 6 Drawing Sheets

SYSTEM AND METHOD FOR ADMINISTERING TWO LIQUIDS

FIELD OF THE INVENTION

This invention relates to a system for administering liquids to a patient; for example medicinal or nutritional liquids in a clinical setting. The liquids may be administered enterally or parenterally. The invention also relates to methods of administering liquids to a patient.

BACKGROUND OF THE INVENTION

Systems for administering liquids to a patient are widely used in clinical settings. All of these systems comprise a container for the liquid and a flow set for delivering the liquid to the patient. In general, the liquid is either allowed to drain through the flow set to the patient under the action of gravity or is pumped through the flow set. Systems using pressure sleeves on the container are also used. Systems using a pump are referred to in this specification as "pump systems".

In many instances, two liquids need to be sequentially administered to the patient. For example, it is often necessary when administering a feeding liquid to periodically flush the system with a flushing liquid to avoid blockages caused by the relatively viscous feeding liquid. Also, it is sometimes necessary to alternatively administer a saline solution and a liquid containing an active agent. In these cases, the system is connected to two containers; each container containing a separate liquid. The system must then switch from one container to the other as needed.

While it is possible to manually switch between the two containers, automatic switching is preferred. Automatic switching may be achieved, for example, by means of a valve actuator unit, such as that disclosed in U.S. Pat. No. 5,584,671, It also possible to separately pump liquid from the two containers using two pumps, each connected to a separate container and each being operated at a different time.

However, there is still a need for a system of sequentially administering two fluids to a patient which is safe, relatively simple, easy to use, and requires only one pump.

SUMMARY OF THE INVENTION

Accordingly, in one aspect, this invention provides a flow set for the sequential administration of two liquids from a pair of containers to a patient, the flow set comprising a pair of valve assemblies each in communication with a container, each valve assembly having three ports communicating through a communication chamber, an inlet port being sealed with a first one-way valve allowing flow of liquid through it only into the chamber, an outlet port being sealed with a second one-way valve allowing flow of liquid through it only out of the chamber, and a pump communication port;

a pair of inlet tubing segments each connecting a container to the inlet port of a valve assembly;

a connecting tubing segment connecting the pump communicating ports of the two valve assemblies; and an outlet tubing segment connected to the outlet port of each valve assembly for delivery of the liquid to the patient.

The flow set provides the advantage of permitting simple and safe switching between the two containers to which the flow set is connected. Liquid may be drawn from one container, into one valve assembly and out through its pump communication port to the other valve assembly through its pump communication port. The liquid then flows out of the outlet port of the other valve assembly to the patient. By merely reversing the pumping direction of a pump connected to the flow set, liquid may be drawn from the other container into the other valve assembly and hence to the patient in a manner mirroring the first. No disconnection of tubing is required and no manual adjustment of valves is required.

Preferably, each first one-way valve permits liquid flow through it only once a pressure differential over the valve exceeds a threshold pressure. Similarly, each second one-way valve preferably permits liquid flow through it only once a pressure differential over the valve exceeds a threshold pressure.

Each one-way valve preferably includes a flexible membrane which is deformable under pressure in a desired flow direction, the flexible membrane having perforations through it which open at a selected extent of deformation of the flexible membrane to permit flow. Each valve assembly may be provided with a support associated with each flexible membrane for preventing the flexible membrane from deforming sufficiently in an opposite flow direction for preventing back flow.

In another aspect, this invention provides a pump system for the sequential administration of two liquids from a pair of containers to a patient, the pump system comprising:

a flow set as defined above; and a pump having a flow path through which the connecting tubing segment extends, the pump being capable of pumping in both directions.

Preferably the pump has a socket defined in its flow path, and the connecting tubing segment has a connecting element of complementary shape to the socket for fitting in the socket upon correct coupling of the pump to the connecting tubing segment.

In a yet further aspect, this invention provides a method for sequentially administering two liquids from a pair of containers to a patient, the method comprising:

operating the pump in one pumping direction for pumping liquid from a first of the containers through a pump system the liquid flowing in a first flow path through the inlet tubing segment connected to the first container to the inlet port of a first of the valve assemblies, out through the pump communication port of the first valve assembly and in the pump communication port of the second of the valve assemblies, out through outlet port of the second valve assembly, and through the outlet tubing segment to the patient; and reversing the pumping direction of the pump for pumping liquid from the second of the containers in a second flow path through the inlet tubing segment connected to the second container to the inlet port of the second valve assembly, out through the pump communication port of the second valve assembly and in the pump communication port of the first valve assembly, out through outlet port of the first valve assembly, and through the outlet tubing segment to the patient.

Preferably the pumping direction of the pump is reversed automatically in accordance with instructions stored within a control unit associated with the pump. The pumping direction of the pump may be reversed at least twice.

BRIEF DESCRIPTION OF THE DRAWINGS

Embodiments of the invention are now described, by way of example only, with reference to the drawings in which.

DETAILED DESCRIPTION OF THE PREFERRED EMBODIMENTS

Figure 1:
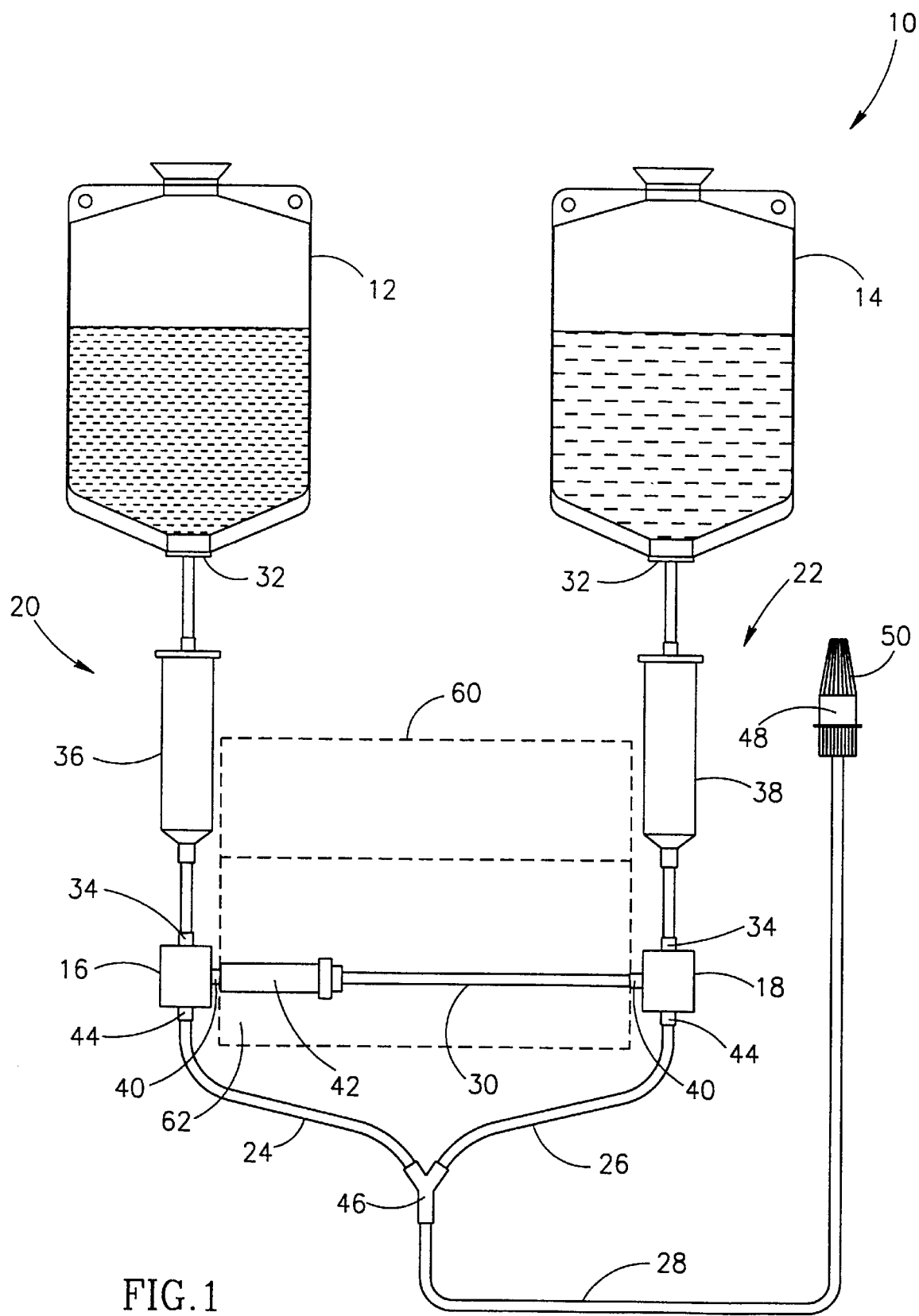
FIG. 1 illustrates a flow set connected to two containers.

A disposable flow set 10 which may be used to sequentially administer two liquids is illustrated in FIG. 1. The flow set 10 is made up of a tubing set, a pair of drip chambers 36, 38, and a pair of valves 16, 18. The tubing set comprises a pair of tube branches which are connected to an administration tube 28 by a Y-connector 46 and which are connected together by a connecting tube 30. The connecting tube 30 is positioned upstream of the Y-connector 46. The free end of the administration tube 28 is connected to a connector 48. As is conventional, the connector 48 may be connected to a catheter, an enteral feeding tube, etc. When not in use, the free end of the connector 48 is covered by a cover 50.

Each tube branch is made up of a pair of first tubing segments 20, 22 and a pair of second tubing segments 24, 26. One end of each first tubing segment 20, 22 is connectable to an outlet 32 of a separate liquid container 12, 14. The other end of each first tubing segment 20, 22 is connected to an inlet 34 of one of the valves 16, 18. The drip chambers 36, 38 are coupled in the first tubing segments 20, 22. One end of each second tubing segment 24, 26 is connected to an outlet 44 of one of the valves 16,18 while the other end is connected to the Y-connector 46. The connecting tube 30 spans between the two valves 16, 18; in each case connecting to a communication port 40 of each valve 16, 18. A shaped connecting element 42 is coupled to the connecting tube 30.

Figure 3A:
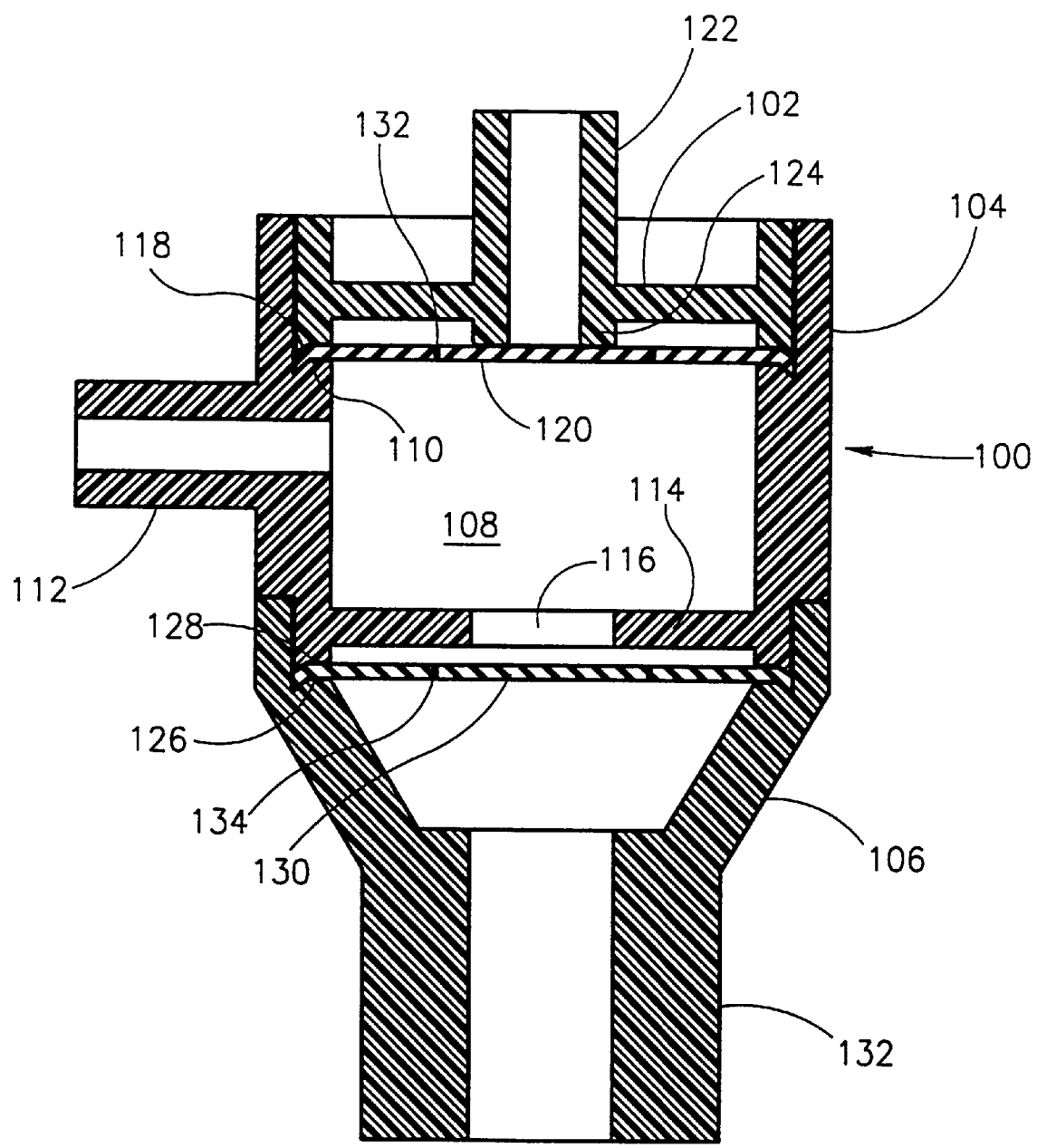
FIG. 3A is a cross-sectional view of a valve in the systems of FIGS. 1 and 2 in a rest state.

Referring now to FIG. 3A, each valve 16, 18 is made up of a housing 100 formed of three body members; a first body member 102, a second body member 104 and a third body member 106. The second body member 104 is in the form of a tube of which the lower end is closed off by a base plate 114. The base plate 114 has an outlet opening 116 through it. The central bore of the second body member 104 forms a chamber 108 above the base plate 114. An annular shoulder 110 is formed in the inner side walls of the second body member 104 near the upper end of the second body member 104. A lateral port 112 extends through the side walls of the second body member 104, between the annular shoulder 110 and the base plate 114. The lateral port 112 forms the communication port 40 to which the connecting tube 30 connects. An annular tab 128 projects away from the lower end of the base plate 114.

The first body member 102 is sized so that at least a portion of it fits snugly into the bore of the second body member 104 to form an upper seal for the chamber 108. The first body member 102 has an annular tab 118 projecting from its lower end. The annular tab 118 has a shape is complementary to the annular shoulder 110 of the second body member 104. In this way, when the first body member 102 is fitted into the second body member 104, the annular shoulder 110 and the annular tab 118 form an annular clamp.

An inlet tube 122 extends through the first body member 102 to define the inlet 34 to the valve 16, 18. The first body member 102 has an annular rim 124 projecting into the chamber 108 about inlet tube 122. A first flexible membrane 120 is clamped between the annular shoulder 110 and the annular tab 118.

The third body member 106 is also in the form of a tube but having the shape of a funnel. An annular shoulder 126 is defined in the side walls of the bore of the third body member 106 near its upper end. The annular shoulder 126 has a shape is complementary to the lower end of the annular tab 128 of the second body member 104. In this way, when the second body member 104 is fitted onto the third body member 106, the annular tab 128 and the annular shoulder 126 form an annular clamp. Further, the annular tab 128 of the second body member 104 is sized to fit snugly in the bore of the third body member 106 to seal the upper end of the third body member 106. An outlet tube 132 extends from the third body member 106 to define the outlet 44 from the valve 16, 18. A second flexible membrane 130 is clamped between the annular tab 128 of the second body member 104 and the annular shoulder 126 of the third body member 106.

The first and second flexible membranes 120, 130 are made of a resilient flexible material, typically a sterilizable material such as silicon, rubber or any suitable material. The membranes 120, 130 each have a plurality of slits 132, 134 (are two shown) which, in the rest state shown in FIG. 3A, are closed and do not permit flow of liquid through the membrane 132, 134. Typically, the membranes 120, 130 are designed so that the slits 132, 134 will open only when the pressure differential over the membrane exceeds about 20 kPa. This prevents undesired free flow of the liquid from the containers 12, 14, which in a clinical setting is typically placed on a stand of a height of about 2 meters.

Figure 2:
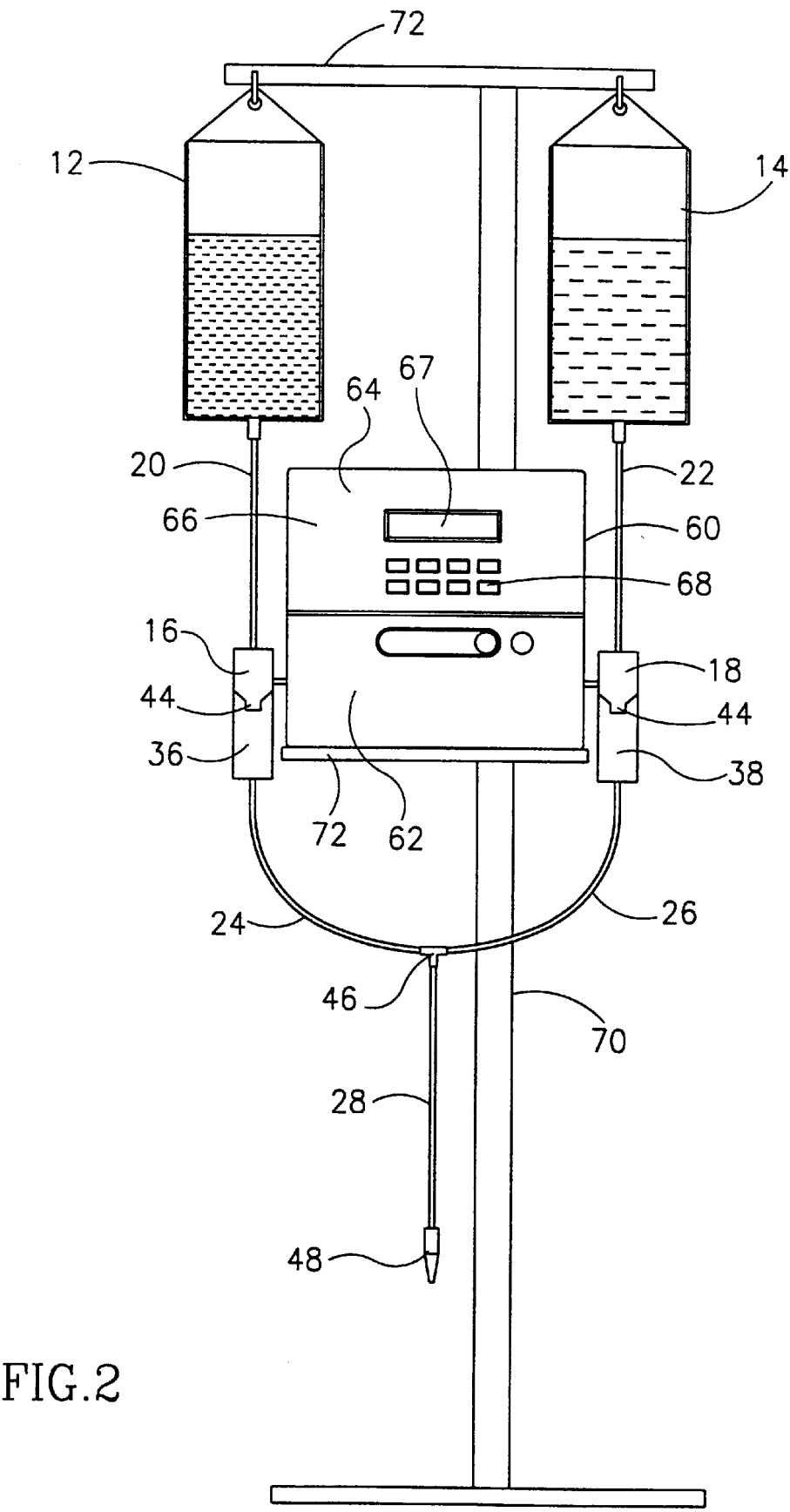
FIG. 2 illustrates a pump system connected to two containers.

A pump 62 of a pump unit 60 (both shown in dotted lines) is coupled to the connecting tube 30 of the flow set 10. The pump 62 is preferably a peristaltic pump but any type of pump which is able to pump liquid at controlled flow rates in both directions and which is suitable for clinical applications may be used. As is best illustrated in FIG. 2, the pump unit 60 may include a control unit 64. The control unit 64 typically comprises a control panel 66 which has a display 67 and a key pad 68. The key pad 68 may be used for manual control of the pump, data entry, and the like. The control unit 64 also includes a microprocessor (not shown) for controlling and activating the pump. A memory (not shown) may be associated with, or be incorporated in, the microprocessor. If desired, the control unit 64 may also include an audio, visual or dual alarm signaling means.

The pump unit 60 has a socket (not shown) which is complementary to the shaped connecting element 42. When the pump system is correctly assembled, the shaped element 42 fits into the socket in the pump unit 60. The pump unit 60 may be provided with a microswitch (not shown) in the socket which generates a signal when the shaped connecting element 42 is fitted in the socket. This signals to the control unit 64 that the pump system has been correctly assembled. The control unit 64 may be programmed not to initiate the pump 62 unless the signal has been received.

As is best illustrated in FIG. 2, the flow set 10 is typically mounted on a stand 70 with the containers 12 and 14 being held by an arm 72 at the top of the stand 70.

A second embodiment of a pump system is shown schematically in FIG. 2. The primary difference between the embodiment of FIG. 2 and that of FIG. 1 is that, in the embodiment of FIG. 2, the drip chambers 36, 38 are coupled to the outlets 44 of the valve 16,18 and not in the first tubing segments 20, 22.

In use, the pump 62 is initiated to pump liquid from one of the containers 12, 14 to a patient. For example, the pump 62 draws liquid from the left hand container 12 of FIG. 1. The liquid is drawn into the first tubing segment 20, through the drip chamber 36, and into the inlet 34 of the valve 16.

Figure 3B:
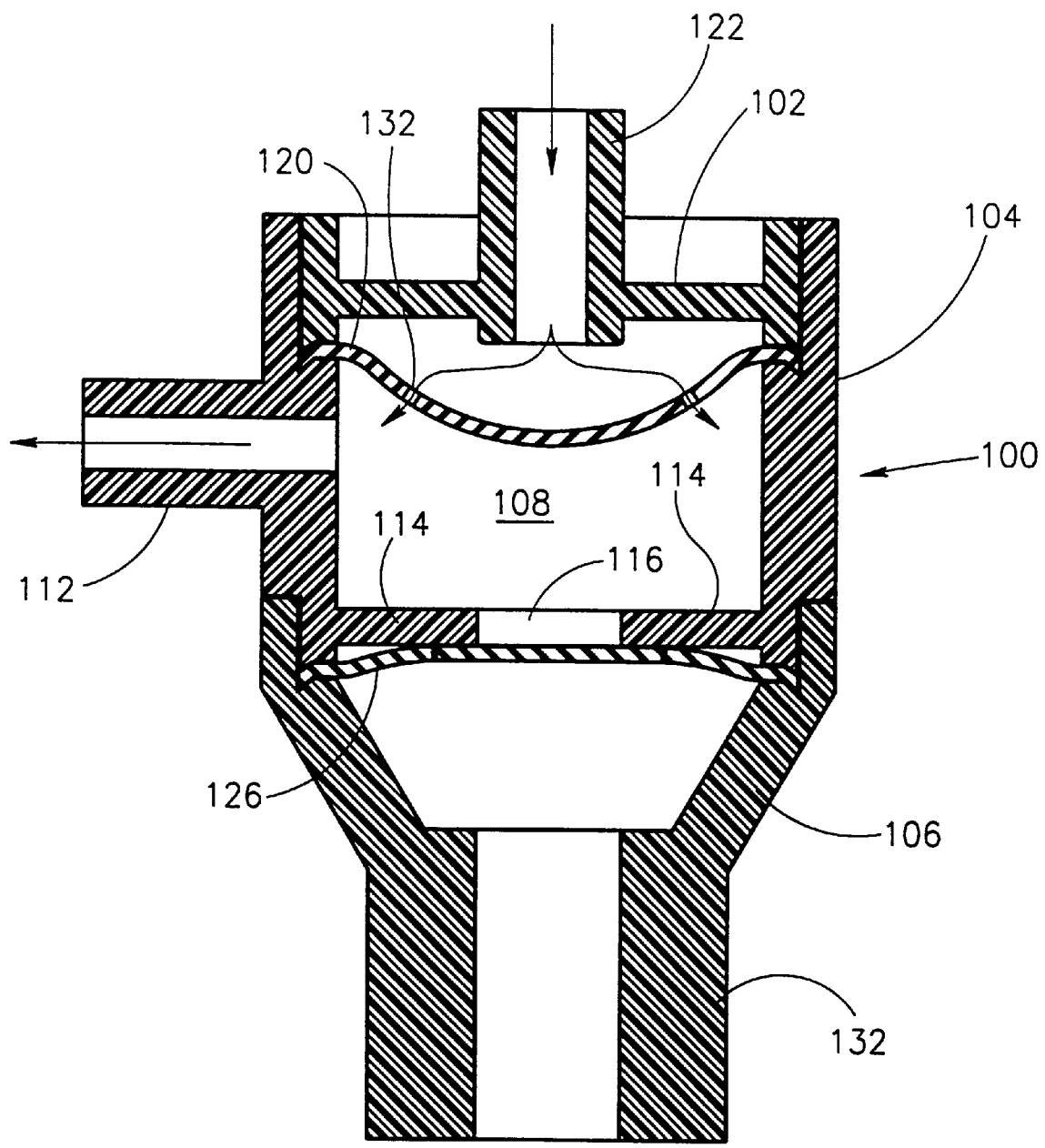
FIG. 3B is a cross-sectional view of the valve in a first operative state.

Prior to the initiation of the pump 62, the valve 16 is in the rest state illustrated in FIG. 3A. When liquid is drawn through the inlet tube 122, the first flexible membrane 120 is stretched and deflected as shown in FIG. 3B. Once the selected threshold pressure differential is reached and the first flexible membrane 120 is sufficiently stretched, the slits 132 in the membrane 120 widen and open to allow flow of liquid from the inlet tube 122 into the chamber 108. Simultaneously, the suction of the pump 62 reduces the pressure in the connecting tube 30 at the feed end of the pump 62 and in the chamber 108 of the valve 16. This causes the second flexible membrane 130 to seal against the base plate 114 of the second body member 104. The liquid entering the chamber 108 then flows from the chamber 108 through the lateral port 112 and into the connecting tube 30. Liquid is unable to penetrate through the second flexible membrane 130.

Figure 3C:
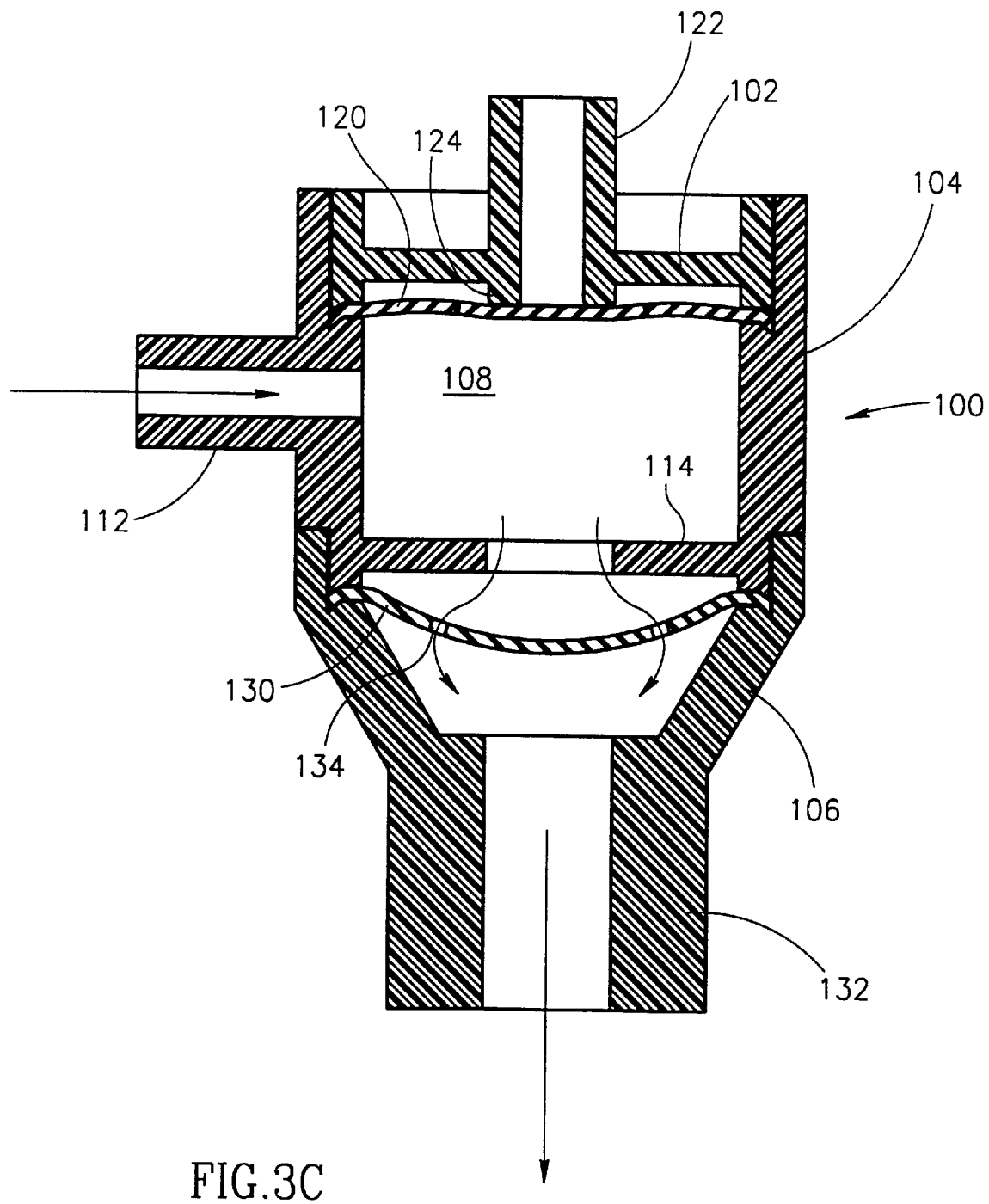
FIG. 3C is a cross-sectional view of the valve in a second operational state.

The liquid is then propelled by the pump 62 to the other valve 18. As best illustrated in FIG. 3C, the liquid enters the valve 18 through the lateral port 112. Once in the camber 108 of the valve 18, the liquid forces the first flexible membrane 120 against the first body member 102. Therefore the first flexible membrane 120 cannot deflect sufficiently to permit liquid flow through it. However, the positive pressure induced in the chamber 108 by the pump 62 causes the second flexible membrane 130 to stretch and deflect. Once the selected threshold pressure differential is reached and the second flexible membrane 130 is sufficiently stretched, the slits 134 in the membrane 130 widen and open to allow flow of liquid from the chamber 108 and out of the outlet tube 132.

Figure 4:
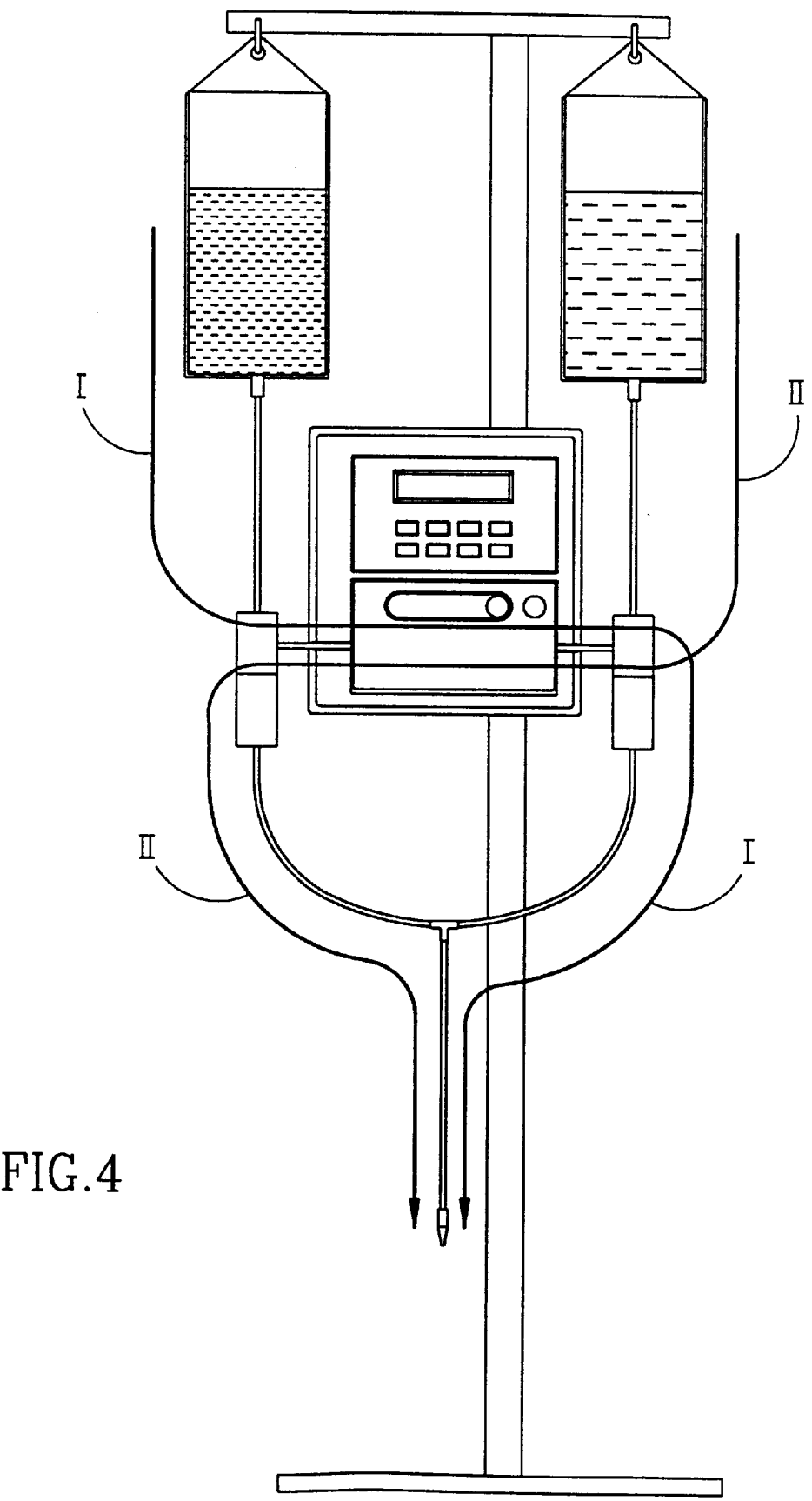
FIG. 4 is a schematic illustration of liquid flow in the system of FIG. 2.

The liquid then flows through the right-hand second tubing segment 26 which is connected to the outlet 44 of the valve, through the Y-connector 46, and into the administration tube 28. A small amount of liquid may initially flow into the left-hand second tubing element 24 but it is prevented from entering the left-hand valve 16 by the second flexible membrane 130 of the left-hand valve 16. Therefore the flow path of the liquid is as illustrated by arrow I in FIG. 4.

Upon wishing to administer the second liquid, the pumping direction of the pump 62 is merely reversed. The flow path of the liquid is as illustrated by arrow II in FIG. 4. The pumping direction of the pump 62 may be reversed manually or automatically at selected times by the control unit 64.

The system therefore provides a safe means of sequentially administering two liquids to a patient which is extremely simple to operate.

It will be appreciated that the system may be operated in various modes. For example, the system may initially flush the flow set 10 with a flushing solution and then switch to a feeding liquid. At selected intervals, the system may then switch back to the flushing solution for a short period to flush the flow set 10 to reduce the probability of blockages.

As another example, the system may deliver a set amount of one liquid to the patient and then deliver a selected amount of the other liquid to the patient. As yet another example, the system may intermittent deliver a set amount of one liquid to the patient and then deliver a selected amount of the other liquid to the patient.

It will be appreciated that numerous modifications may be made to the preferred embodiments without departing from the scope of the invention as set out in the claims. For example, it is not essential for drip chambers 36,38 to be connected in the flow set 10. It is also not essential to provide the pump 62 with a socket and the connecting tube 30 with a shaped connecting element 42. Similarly, the Y-connector 46 may be replaced with any suitable connector. Similarly, the flow set need not use the valves 16, 18 described above. Other valve arrangements may be used; for example each valve 16, 18 may be replaced with an assembly of a pair of one way valves which open upon a threshold pressure being reached. The connecting tube 30 will then extend from a position between the pair of one way valves of each assembly.

I claim:

1. A flow set for the sequential administration of two liquids from a pair of containers to a patient, the flow set comprising
   a pair of valve assemblies each in communication with a container, each valve assembly having three ports communicating through a communication chamber, an inlet port being sealed with a first one-way valve allowing flow of liquid through it only into the chamber, an outlet port being sealed with a second one-way valve allowing flow of liquid through it only out of the chamber, and a pump communication port;
   a pair of inlet tubing segments each connecting a container to the inlet port of a valve assembly;
   a connecting tubing segment connecting the pump communicating ports of the two valve assemblies; and
   an outlet tubing segment connected to the outlet port of each valve assembly for delivery of the liquid to the patient.

2. A flow set according to claim 1 in which each first one-way valve permits liquid flow through it only once a pressure differential over the valve exceeds a threshold pressure.

3. A flow set according to claim 2 in which each second one-way valve permits liquid flow through it only once a pressure differential over the valve exceeds a threshold pressure.

4. A flow set according to claim 1 in which each one-way valve includes a flexible membrane which is deformable under pressure in a desired flow direction, the flexible membrane having perforations through it which open at a selected extent of deformation of the flexible membrane to permit flow.

5. A flow set according to claim 4 in which each valve assembly has a support associated with each flexible membrane for preventing the flexible membrane from deforming sufficiently in an opposite flow direction for preventing back flow.

* * * * *